(12) United States Patent
Crawford

(10) Patent No.: US 8,399,854 B1
(45) Date of Patent: Mar. 19, 2013

(54) COMBINATION SCALE AND GERMICIDAL STERILIZATION APPARATUS

(76) Inventor: Derek G. Crawford, Hamlet, NC (US)

( * ) Notice: Subject to any disclaimer, the term of this patent is extended or adjusted under 35 U.S.C. 154(b) by 0 days.

(21) Appl. No.: 13/216,320

(22) Filed: Aug. 24, 2011

(51) Int. Cl.
*G01N 23/00* (2006.01)
*H01J 37/20* (2006.01)
*A21D 6/00* (2006.01)
*A61L 2/00* (2006.01)

(52) U.S. Cl. ............. 250/455.11; 250/461.1; 426/248; 422/24; 422/186.3

(58) Field of Classification Search ............. 250/372, 250/453.11, 454.11, 455.11, 458.1, 459.1, 250/461.1, 492.1, 504 H, 504 R, 519.1, 522.1, 250/526; 426/234, 237, 248; 422/22, 24, 422/120, 121, 186.3
See application file for complete search history.

(56) References Cited

U.S. PATENT DOCUMENTS

| | | | | |
|---|---|---|---|---|
| 3,535,513 | A * | 10/1970 | Cirami | 250/430 |
| 3,906,236 | A * | 9/1975 | Callahan | 250/455.11 |
| 4,868,397 | A * | 9/1989 | Tittel | 250/455.11 |
| 4,896,042 | A * | 1/1990 | Humphreys | 250/435 |
| 5,029,252 | A * | 7/1991 | Ameseder | 250/455.11 |
| 5,348,704 | A * | 9/1994 | Tanaka | 422/22 |
| 5,597,597 | A | 1/1997 | Newman | |
| 6,461,568 | B1 | 10/2002 | Eckhardt | |
| 6,586,172 | B1 | 7/2003 | Gunn et al. | |
| 6,730,265 | B2 | 5/2004 | Horton, III | |
| 6,953,940 | B2 * | 10/2005 | Leighley et al. | 250/455.11 |
| 7,326,387 | B2 * | 2/2008 | Arts et al. | 422/186.3 |
| 7,575,770 | B2 | 8/2009 | Garwood | |
| 2001/0042842 | A1 * | 11/2001 | Leighley et al. | 250/504 H |
| 2005/0276720 | A1 | 12/2005 | Correa | |
| 2007/0212273 | A1 * | 9/2007 | Edwards | 422/186.3 |
| 2008/0199353 | A1 * | 8/2008 | Mlodzinski et al. | 422/24 |
| 2008/0310996 | A1 | 12/2008 | Kim et al. | |
| 2009/0180933 | A1 * | 7/2009 | Kauling et al. | 422/82.08 |
| 2009/0314308 | A1 | 12/2009 | Kim et al. | |
| 2010/0104470 | A1 * | 4/2010 | McCabe | 422/22 |
| 2010/0183779 | A1 * | 7/2010 | Felix | 426/231 |
| 2010/0260644 | A1 | 10/2010 | Day et al. | |
| 2011/0174992 | A1 * | 7/2011 | Sakita | 250/492.1 |

\* cited by examiner

*Primary Examiner* — Bernard E Souw
(74) *Attorney, Agent, or Firm* — P. Jeff Martin; The Law Firm of P. Jeffrey Martin, LLC

(57) ABSTRACT

A germicidal sterilization apparatus which includes a housing, a plate disposed atop the housing, and at least one ultraviolet light source supported by the housing. The at least one UV light source is adapted and configured to generate UV light waves which kill or deactivate harmful germs, microorganisms and spores thereof, pathogens, and/or transmissible diseases. The apparatus is integrated with a weight-measuring device for determining and indicating the weight of an individual.

26 Claims, 7 Drawing Sheets

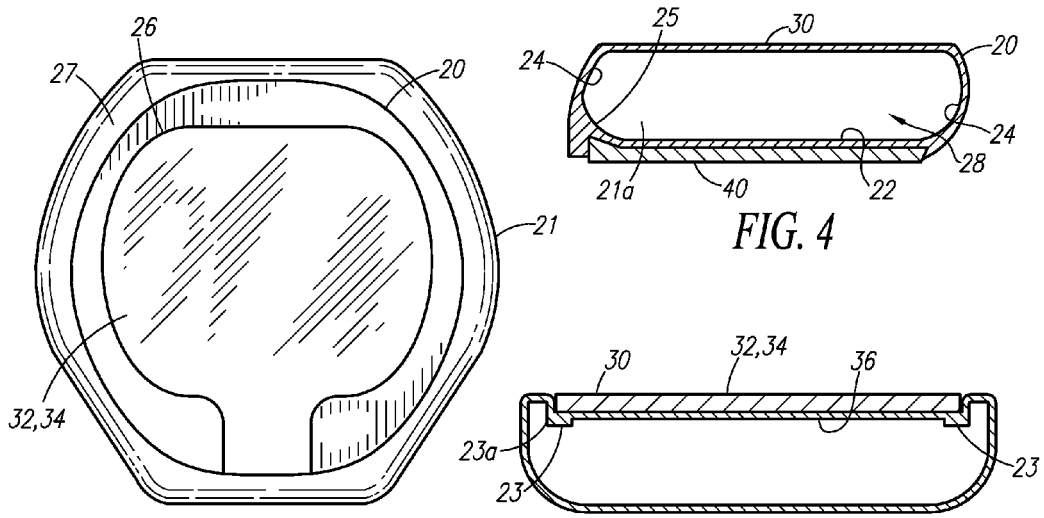
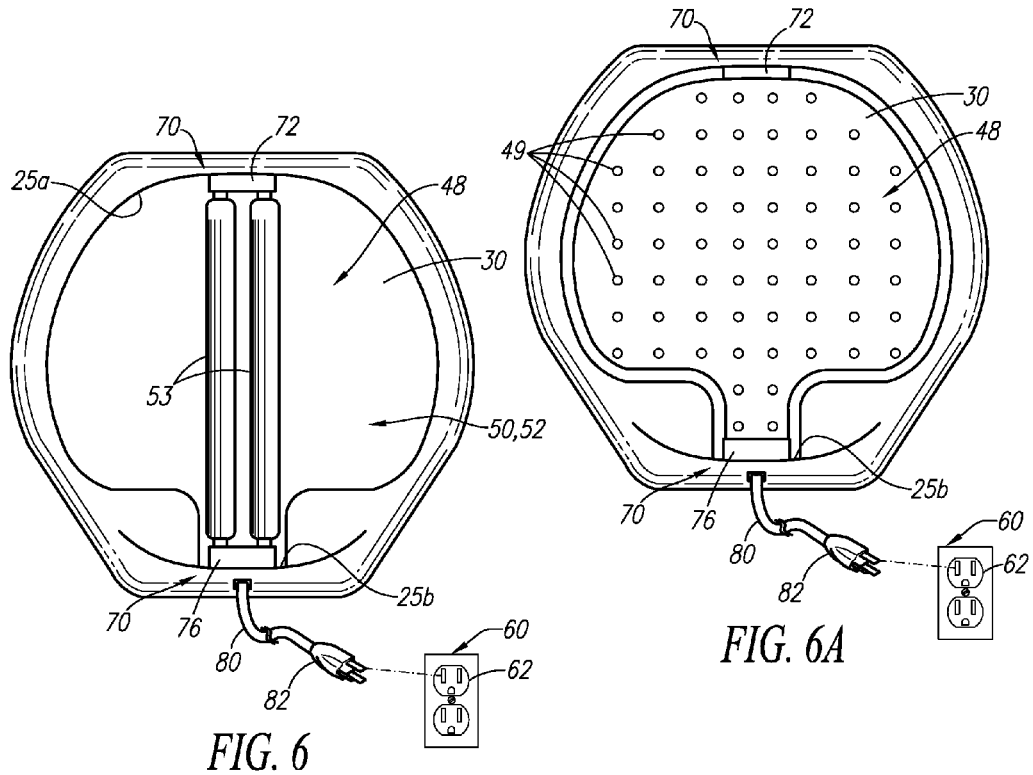

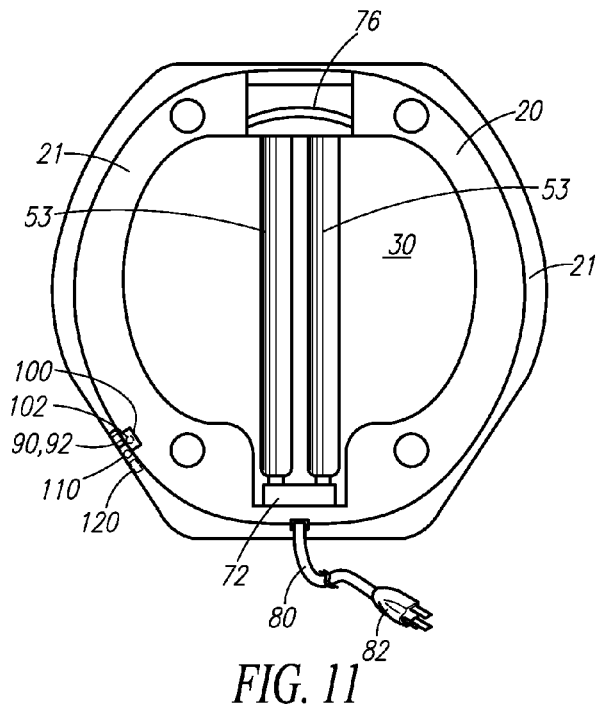
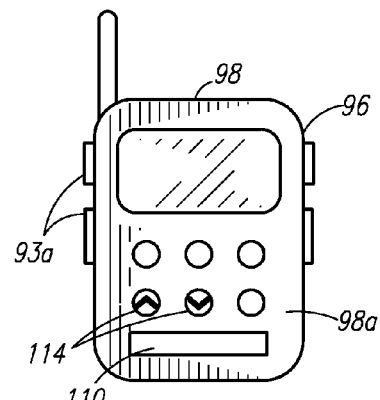
FIG. 11
FIG. 13
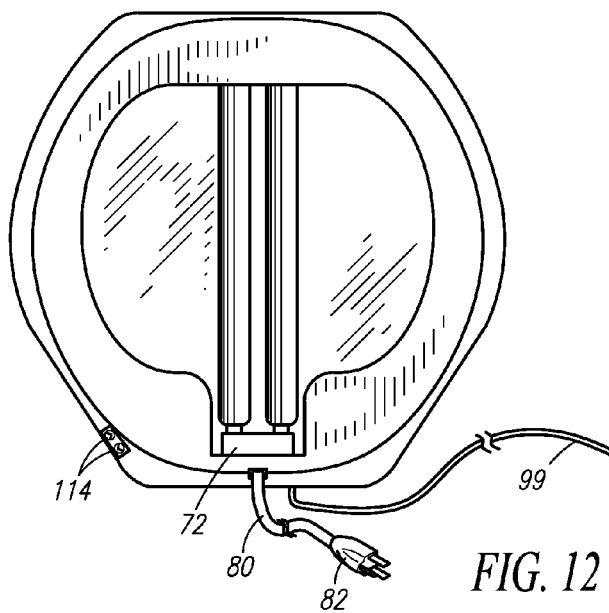
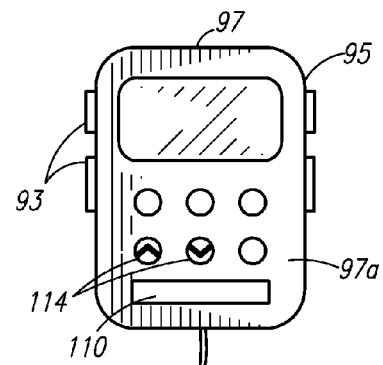
FIG. 12

COMBINATION SCALE AND GERMICIDAL STERILIZATION APPARATUS

RELATED APPLICATIONS

There are no previously filed, nor currently any co-pending applications, anywhere in the world.

BACKGROUND OF THE INVENTION

1. Field of the Invention

The present invention relates generally to devices for sterilizing objects and articles using ultraviolet radiation and, more particularly, to a combination scale and germicidal sterilization apparatus.

2. Description of the Related Art

For a number of years, scientists have known that natural sunlight is one of the most effective air purifiers. The sun's ultraviolet C (UV-C) rays act as a natural outdoor air purification system, inhibiting the growth and reproduction of bacteria, viruses, molds, and fungi.

UV-C light is germicidal, meaning it deactivates the DNA of bacteria, viruses, dust mites, molds, fungi, and other pathogens, thereby destroying their ability to reproduce and cause disease. UV-C causes damage to the nucleic acid of microorganisms by forming covalent bonds between certain adjacent bases in the DNA. The formation of such bonds prevent the DNA from being unzipped for replication (cell division), rendering the organism unable to reproduce. Being unable to replicate, the organism dies.

There are four principal wavelengths in the ultraviolet spectrum. These principal wavelengths consist of UV-A, UV-B, UV-C, and extreme shortwave UV Energy, which generates ozone.

UV-A is a normal component of sunlight and has a wavelength range from 315 nanometers (nm) to 400 nm. It has a relatively longer wavelength with respect to the other ultraviolet light, thereby allowing it to penetrate the atmosphere.

UV-B is found in the middle wavelength region of the ultraviolet spectrum. It has a wavelength range from 280 nm to 315 nm.

UV-C is shortwave ultraviolet radiation. It has a wavelength range from 100 nm to 280 nm.

Extreme shortwave UV Energy has a wavelength range from 10 nm to 121 nm.

UV-C is a magnetic waveform, and like all waveforms emanating from the sun, UV-C's properties are unique to its frequency. UV-C energy has germicidal affects. A microorganism's DNA is the target of the 253.7 nm wavelength. UV-C energy destroys DNA causing cell death or making replication impossible. Thus, UV-C light with a wavelength of approximately between 250 to about 260 nm provides the highest germicidal effectiveness. Generally, exposure to UV energy for about 20 to about 34 milliwatt-seconds/cm$^2$ is suitable to deactivate approximately 99 percent of bacteria, viruses, and other pathogens.

While the prior art discloses various devices and systems utilizing UV radiation for sterilizing objects and various articles, it is silent regarding a germicidal sterilization apparatus incorporating a weight-measuring device.

Accordingly, a need exists for a combination scale and germicidal sterilization apparatus. The development of the germicidal sterilization apparatus fulfills this need.

A search of the prior art did not disclose any patents that read directly on the claims of the instant invention; however, the following references were considered related:

U.S. Pat. No. 6,461,568 B1, issued in the name of Eckhardt;
U.S. Patent Application no. 2008/0310996 A1, published in the name of Kim et al.;
U.S. Patent Application no. 2009/0314308 A1, published in the name of Kim et al.;
U.S. Pat. No. 7,575,770 B2, issued in the name of Garwood;
U.S. Pat. No. 5,597,597, issued in the name of Newman;
U.S. Pat. No. 6,730,265 B2, issued in the name of Horton, III;
U.S. Patent Application no. 2010/0260644 A1, published in the name of Day et al.;
U.S. Pat. No. 6,586,172 B1, issued in the name of Gunn et al.; and
U.S. Patent Application no. 2005/0276720 A1, published in the name of Correa et al.

Consequently, a need has been felt for a combination scale and germicidal sterilization apparatus. This application presents claims and embodiments that fulfill a need or needs not yet satisfied by the products, inventions and methods previously or presently available. In particular, the claims and embodiments disclosed herein describe a germicidal sterilization apparatus comprising a housing, a plate secured to or formed integral with the housing for supporting an individual thereatop, a base plate, at least one ultraviolet light source supported by the housing, control electronics, and a weight-measuring device; the apparatus of the present invention providing unanticipated and nonobvious combination of features distinguished from the products, inventions and methods pre-existing in the art. The applicant is unaware of any product, device, method, disclosure or reference that discloses the features of the claims and embodiments disclosed herein.

SUMMARY OF THE INVENTION

Briefly described according to one embodiment of the present invention, a germicidal sterilization apparatus is disclosed. The apparatus comprises a housing, a plate secured to or formed integral with the housing for supporting an individual thereatop, a base plate, and at least one electromagnetic light source, such as an ultraviolet (UV) light source, supported by the housing. The at least one UV light source is adapted and configured to generate UV light waves which kill or deactivate harmful germs, microorganisms and spores thereof, pathogens, and/or transmissible diseases, thereby preventing the harmful germs, microorganisms and spores thereof, pathogens, and/or transmissible diseases from spreading and causing harm to other individuals.

The housing comprises a vessel wall having a bottom from which an arched sidewall extends upwardly therefrom forming a hollow interior defined as a UV light source cavity within which the at least one UV light source is enclosed.

The plate is UV-transparent or UV-transmissive, and suitably rigid and durable so as to support individuals thereatop. The plate includes an upper surface defined as a target surface opposing a lower surface.

A power source powers the at least one UV light source. The at least one UV light source is removably held within and in electrical connection with a UV lamp holder.

Activation of the at least one UV light source is selectively-controlled by control electronics. The control electronics comprises an ON/OFF switch for energizing and de-energizing the at least one UV light source.

The control electronics may comprise a motion detector configured to detect when a user places his/her feet atop the plate. The control electronics may further comprise a timer configured to de-energize the at least one UV light source upon the expiration of a predetermined interval of time.

The apparatus of the present invention further comprises an electronic weight-measuring device for determining and indicating the weight of an individual. The weight-measuring device includes a weight sensor, and an electronic unit.

An alternate embodiment of the present invention is disclosed, wherein the alternate embodiment comprises a germicidal sterilization apparatus comprising a housing, a plate secured to or formed integral with the housing for supporting an individual thereatop, a base plate, and at least one electromagnetic light source, such as a UV light source, supported by the housing. The apparatus of the alternate embodiment further comprises a central processing unit, memory and a storage device(s). The apparatus includes a power source for supplying power to operate the apparatus.

The plate is more specifically defined as a touch sensitive plate configured to allow a user to activate the at least one UV light source by engaging (pressing/deforming) the plate using a finger or a stylus.

The apparatus of the alternate embodiment may further comprise a weight-measuring device, the weight-measuring device being activated by engaging the plate using a finger or a stylus.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 3 is a top plan view of the apparatus of FIG. 1;

FIG. 4 is a cross-sectional view of the apparatus of FIG. 1, illustrating the UV light source cavity thereof;

FIG. 5 is a cross-sectional view of the housing of a germicidal sterilization apparatus showing a flange for supporting the plate, in accordance to one embodiment of the present invention;

FIG. 6 is a top plan view of the germicidal sterilization apparatus, illustrating the UV lamp holder thereof, according to one embodiment of the present invention;

FIG. 6A is a top plan view of a light therapy apparatus shown housing an array of infrared LEDs;

FIG. 11 is a top plan view of the germicidal sterilization apparatus illustrating the control electronics, in accordance to one embodiment of the present invention;

FIG. 12 is a perspective view of the germicidal sterilization apparatus, wherein the control electronics have been provided in a remote, wired hand-held device, according to one embodiment of the present invention;

FIG. 13 is a perspective view of a remote, wireless hand-held device which includes control electronics, according to one embodiment of the present invention;

DESCRIPTION OF THE PREFERRED EMBODIMENT

Detailed Description of the Figures

Figure 1:
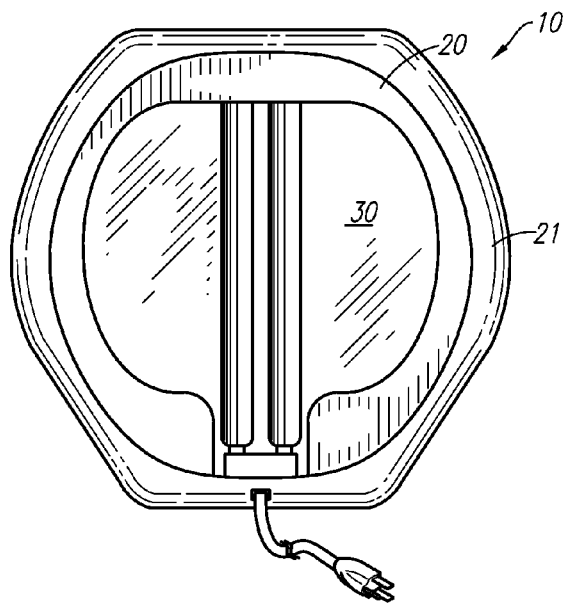
FIG. 1 is a perspective view of a germicidal sterilization apparatus, according to one embodiment of the present invention.
Figure 2:
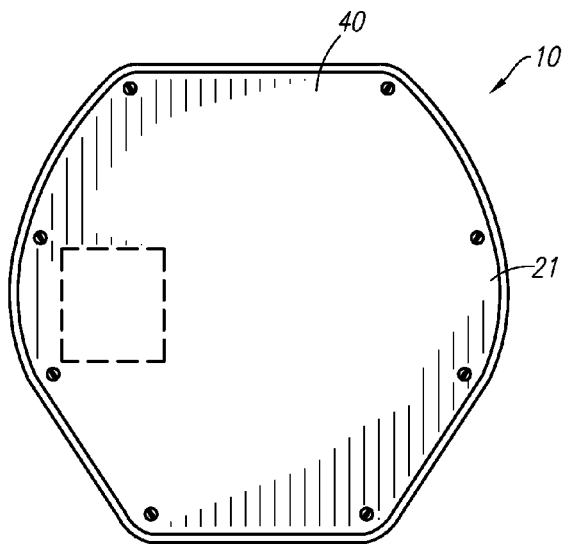
FIG. 2 is a bottom plan view of the apparatus of FIG. 1, illustrating the base plate thereof.

Referring now to FIGS. 1-4, and 6, a germicidal sterilization apparatus 10 is shown, according to one embodiment of the present invention.

The germicidal sterilization apparatus 10 generally comprises a housing 20, a planar plate 30 secured to or formed integral with the housing 20 for supporting an individual thereatop, a base plate 40, and at least one electromagnetic light source 48, such as at least one ultraviolet (UV) light source 50, supported by the housing 20.

The housing 20 is constructed of a lightweight, rigid material selected from the group comprising plastic, plastic polymer, thermoplastic, metal or a metallic-plastic composite. Preferred plastic, plastic polymer or thermoplastic materials include polyvinyl chloride (PVC), polypropylene, polyolefin, acrylonitrile-butadiene-styrene (ABS), polyethylene, polyurethane, polycarbonate, or blends thereof, and ABS/Nylon blend. The housing 20 may fabricated utilizing a common molding process such as injection molding, blow molding, extrusion, or other molding and fabricating methods. A preferred metal construction material is aluminum.

The at least one UV light source 50 is adapted and configured to generate UV light waves which kill or deactivate harmful germs (e.g., bacteria, viruses, mold, fungi, parasites, and spores thereof), microorganisms and spores thereof, pathogens, and/or transmissible diseases, thereby preventing the harmful germs, microorganisms and spores thereof, pathogens, and/or transmissible diseases from spreading and causing harm to other individuals.

In reference to FIG. 6A, in accordance to one embodiment, it is contemplated the at least one electromagnetic light source 48 comprises an array of infrared (IR) light emitting diodes (LEDs) 49 which emit IR light at a wavelength range of approximately 500 nm to 1,100 nm. The IR light is administered to patients to prevent scar tissue formation, inflammation, and degenerative osteoarthritis. In addition, the IR light promotes wound healing and pain relief for scars, arthritis, fibromyalgia, sprains, headaches, diabetic ulcers, neuralgia, bursitis, sinsusitis, tennis elbow, Temporomandibular joint disorder (TMJ), Carpal Tunnel, inflammation, edema, skin care, and the like. The use of IR light therapy also aids in preventing bone and muscle atrophy. IR light at a wavelength of 660 nm penetrates human tissue to a depth of about 8-10 millimeters (mm). Thus, IR light at a wavelength of 660 nm is very beneficial in treating problems close to the surface of the skin such as wounds, cuts, scars, and infection. IR light at a wavelength of 880 nm penetrates human tissue to a depth of about 30-40 mm, thereby being more effective for bones, joints and deep muscle problems.

The housing 20 is fixedly connected to the base plate 40. The housing 20 comprises a vessel wall 21 having a bottom 22 from which an arched sidewall 24 extends upwardly therefrom. The bottom 22 and arched sidewall 24 include a UV reflective interior surface 25 and/or coating. The UV reflective interior surface 25 may be constructed of a UV reflective material selected from the group which includes, but is not limited to reflective metals and alloys, such as aluminum and stainless steel. Alternatively, or in addition to the reflective metals, non-metallic UV reflective materials may be utilized. The area 21a between the UV reflective interior surface 25 and the plate 30 forms a UV light source cavity 28 within which the at least one UV light source 50 is enclosed.

While the housing 20 is illustrated herein as having a generally circular configuration, the housing 20 may comprise a number of geometric shapes, such as, but not limited to oval, square, rectangular, triangular, pentagonal, hexagonal, octagonal, and the like.

The plate 30 is UV-transparent or UV-transmissive, and suitably rigid and durable so as to support individuals thereatop. The plate 30 includes an upper surface 32 defined as a target surface 34 opposing a lower surface 36. The plate 30 is disposed atop the housing 20 and is shaped and configured to match the shape and configuration of a continuous interface 26 of the housing 20, the interface 26 joining the UV reflective interior surface 25 and outer circumferential surface 27 of arched sidewall 24 of housing 20. In one embodiment, the plate 30 may be suitably mounted against interface 26 or interior surface 25, or removably securable to the interface 26 and/or interior surface 25 in a detachably, snap-fit manner.

In reference to FIG. 5, in accordance to another embodiment, the UV reflective interior surface 25 may include a radially extending flange 23, the flange 23 integrally extends orthogonally from the interface 26 about an entire perimeter thereof, the flange 23 providing a support ledge or lagging 23a to which plate 30 is suitably mounted or removably secured in a detachably, snap-fit manner.

Referring now more specifically to FIGS. 1, 4, and 6-7, a power source 60 powers the at least one UV light source 50 and provides electrical input necessary for operating the apparatus 10. The at least one UV light source 50 is removably held within and in electrical connection with a UV lamp holder 70. The UV lamp holder 70 comprises a first lamp coupling 72 and a second lamp coupling 76 for receiving respective opposing ends of the at least one UV light source 50. The first lamp coupling 72 and second lamp coupling 76 are suitably mounted to opposing sidewalls 25a and 25b of the UV reflective interior surface 25.

In accordance to one embodiment of the present invention, the UV lamp holder 70 is electrically connected to a power cord 80 and power cord plug 82, the plug 82 is receivable within a standard electrical wall outlet 62 in order to electrically couple the UV lamp holder 70 to a source of electrical power 60, and thereby powering the at least one UV light source 50.

Figure 7:
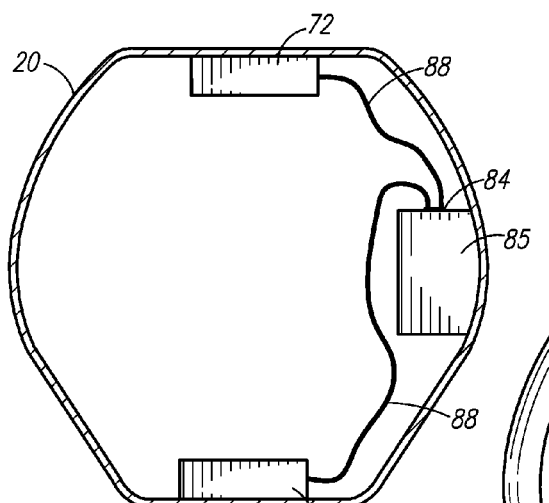
FIG. 7 is top side cross-sectional view of the germicidal sterilization apparatus, illustrating an alternative power source, according to one embodiment of the present invention.
Figure 8:
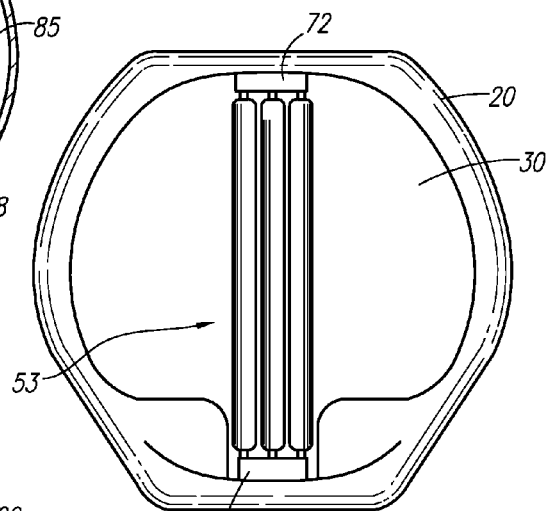
FIG. 8 is a top plan view of the germicidal sterilization apparatus utilizing UV-C lamp tubes, according to one embodiment of the present invention.
Figure 9:
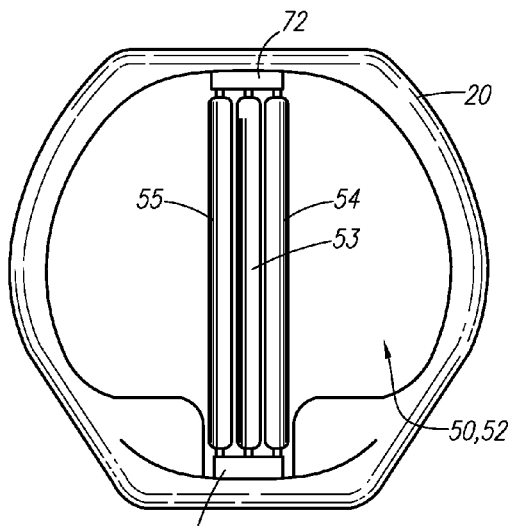
FIG. 9 is a top plan view of the germicidal sterilization apparatus utilizing a combination of UV-A, UV-B, and UV-C lamp tubes, according to one embodiment of the present invention.
Figure 10:
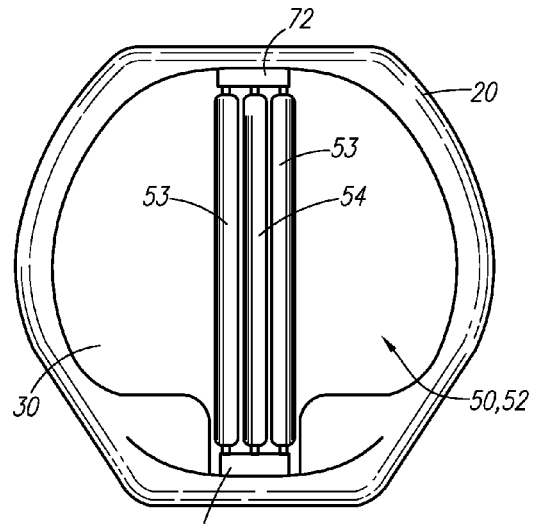
FIG. 10 is a top plan view of the germicidal sterilization apparatus utilizing a combination of UV-A and UV-C lamp tubes, according to one embodiment of the present invention.

Referring more specifically to FIG. 7, in accordance to another embodiment of the present invention, power source 60 is a rechargeable battery 84 or series of batteries to which the UV lamp holder 70 is electrically connected via wiring 88. Accordingly, the rechargeable battery 84 may include a battery receiver 85 within the housing 20 to hold the battery 84 or batteries which may be utilized as a source of electrical power 60.

Power source 60 may be solar powered, or some other suitable means for providing the electrical input required to power and operate the at least one UV light source 50.

It is envisioned the present invention may include an embodiment comprising a power cord 80 and power cord plug 82 for receipt by a standard electrical wall outlet 62, and a rechargeable battery 84 or series of batteries, thus providing the apparatus 10 of the present invention with multiple power source options.

Referring now to FIGS. 1-4, and more particularly to FIGS. 11-13, activation of the at least one UV light source 50 is selectively-controlled by control electronics 90. The control electronics 90, in accordance to one embodiment, comprises a manual ON/OFF switch 92. Actuation of the ON/OFF switch 92 to an "ON" position causes switch 92 to generate a signal to electrically energize the at least one light source 50. Conversely, actuation of the ON/OFF switch 92 to an "OFF" position causes switch 92 to generate a signal to de-energize the at least one UV light source 50. The ON/OFF switch 92 may be suitably mounted to the vessel wall 21 in a location easily accessible by user. Alternatively, ON/OFF switch 93 or 93a may be provided in the form of a remote, wired hand-held device 95, or a remote, wireless hand-held device 96, respectively. With respect to an embodiment incorporating the wired hand-held device 95, such device 95 is configured so as to be in electrical communication, via wiring 99, with the at least one UV light source 50 to facilitate activation and deactivation thereof. With respect to an embodiment incorporating the wireless hand-held device 96, such device 96 is configured so as to be in wireless, electrical communication with the at least one UV light source 50 to facilitate activation and deactivation thereof.

The control electronics 90 may comprise a motion detector 100 configured to detect when a user places his/her feet atop the plate 30. The motion detector 100 comprises an automatic switch 102, whereupon detection of the presence of a user's feet atop plate 30, the automatic switch 102 generates a signal to electrically energize the at least one UV light source 50. The motion detector may be actuated to override the manual ON/OFF switch 92 by depressing a switch mode button 110. Depression of switch mode button 110 allows user to select manual or automatic activation of the at least one light source 50 in an alternating, selectively-desired manner. Switch mode button 110 may be disposed along the vessel wall 21 of housing 20, or on a wall 97a, 98a of hand-held device housing 97, 98 of hand-held device 95, 96, respectively.

The control electronics 90 may further comprise a timer 120 configured to de-energize (or deactivate) the at least one UV light source 50 upon the expiration of a predetermined interval of time, e.g., 25 seconds, wherein the predetermined interval of time may be selectively set by user or operator via a plurality of interval control buttons 114.

Referring now to FIGS. 1, and 6-13, in accordance to the preferred embodiment, the at least one UV light source 50 comprises a plurality of UV lamp tubes 52 removably held within the UV lamp holder 70. When activated, the UV lamp tubes 52 generate UV light waves which are directed and reflected from the UV light source cavity 28 toward and through the target surface 34 of plate 30. The emitted UV light waves kill or deactivate harmful germs, microorganisms and spores thereof, pathogens and/or transmissible diseases disposed on the target surface 34 of plate 30, and more particularly, emitted UV light waves kill or deactivate harmful germs or transmissible diseases carried by the user's feet, socks or shoes worn by the user standing atop plate 30.

In particular, by way of example and not of limitation, one preferred embodiment according to the present invention employs two UV lamp tubes 52, wherein the UV lamp tubes 52 are more specifically defined as UV-C lamp tubes 53. As shown in FIG. 6, the first lamp coupling 72 and the second lamp coupling 76 are configured to removably hold the two UV-C lamp tubes 53. In reference to FIG. 8, the first lamp coupling 72 and second lamp coupling are shown supporting three UV-C lamp tubes 53. Thus, for purposes of the present application, the UV lamp holder 70 may be adapted and configured for holding a selectively-desired number of UV lamp tubes 52.

In addition, in one embodiment, the at least one UV light source 50 may comprise UV lamp tubes 52 which include UV-C lamp tubes 53 in combination with other UV lamp tubes 52, such as UV-A lamp tubes 54 and/or UV-B lamp tubes 55.

Upon activation, the UV lamp tubes 52 generate UV light waves which are directed and reflected from the UV light source cavity 28 toward and through the plate 30, thereby sterilizing the target surface 34 and the user's feet, socks or shoes worn by the user standing atop plate 30.

Figure 14:
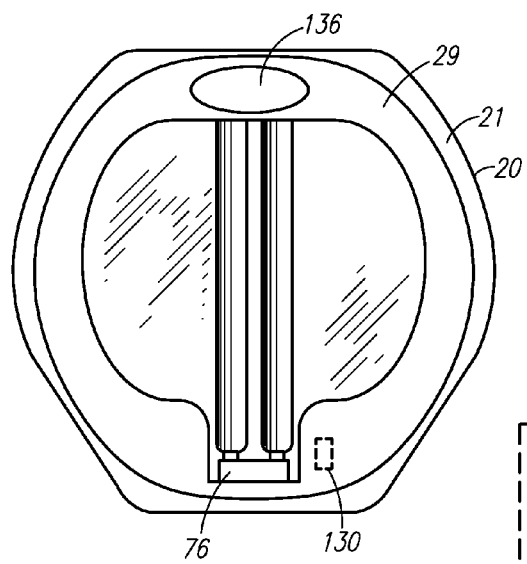
FIG. 14 is top plan view of a germicidal sterilization apparatus integrated with an electronic weight-measuring device, according to one embodiment of the present invention.
Figure 15:
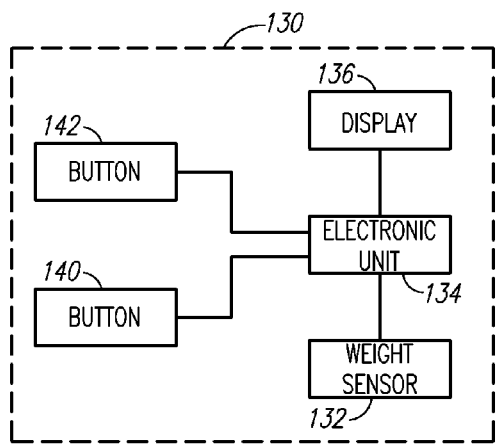
FIG. 15 is a block diagram of the weight-measuring device of FIG. 14.
Figure 16:
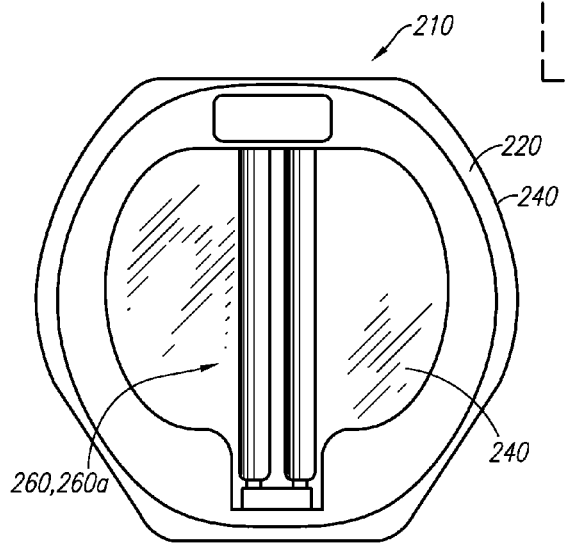
FIG. 16 is top plan view of a germicidal sterilization apparatus, according to an alternate embodiment of the present invention.
Figure 17:
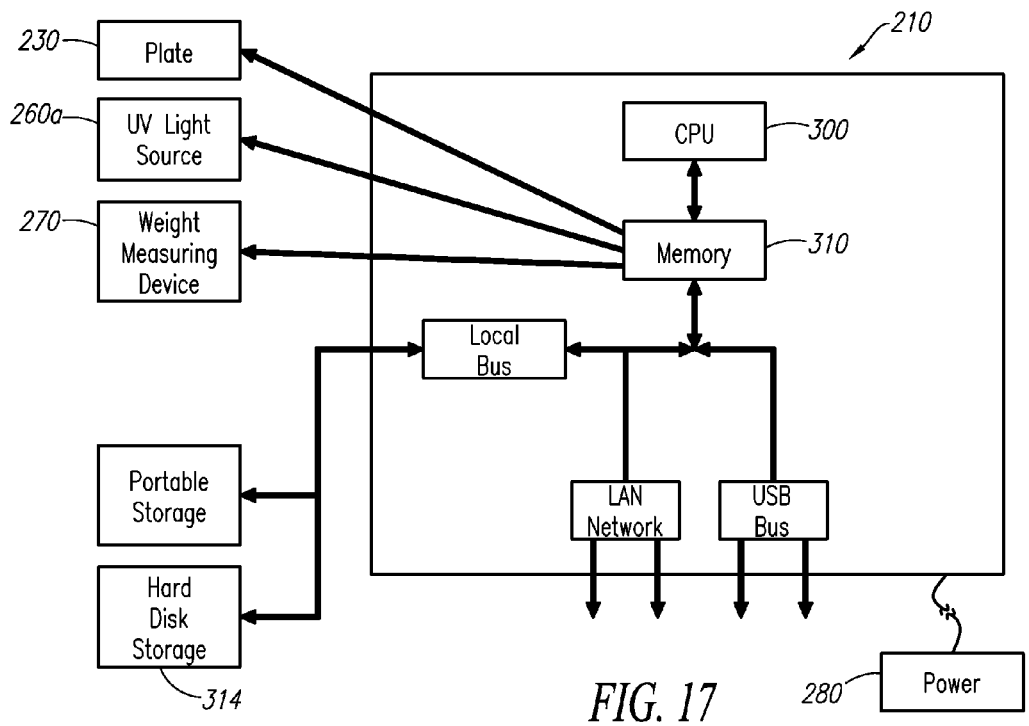
FIG. 17 is a schematic diagram of the electronics and computing technology of the alternate embodiment of FIG. 16, as described in the description below.
Figure 18:
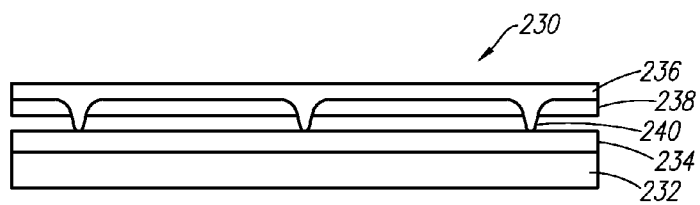
FIG. 18 is a side elevational view showing a portion of the plate, in accordance to the alternate embodiment.

Referring now more specifically to FIGS. 14-15, an electronic weight-measuring device 130 for determining and indicating the weight of an individual is provided. The weight-measuring device 130 comprises a weight sensor 132, and an electronic unit 134. The weight-measuring device 130 is disposed along a lower surface of the arched sidewall 24 of housing 20, proximal to second lamp coupling 76 of UV lamp holder 70. The weight sensor 132 may be any suitable transducer having a property that changes in proportion to the weight applied thereto. Such a weight-dependent property may be, e.g., resistance, or any other physical property. The electronic unit 134 obtains and processes the weight-dependent property of the weight sensor 132 in order to determine the weight of the individual.

The weight-measuring device 130 includes a display 136 fitted in an upper vessel wall portion 29 of housing 20. The display 136 displays the weight of the individual. The electronic unit 134 outputs appropriate signals to the display 136 in order to display the weight of the individual.

The electronic unit 134 may be constructed from modest components, but alternatively could include a suitable microcontroller or microprocessor. The electronic unit 134 is preferably constructed so as to indicate it has completed determining the weight of the individual, and that the weight reading currently displayed on the display 136 is fixed and is the correct weight of the individual. Upon individual stepping off the apparatus 10, the electronic unit 134 automatically resets to obtain a new weight determination.

The weight-measuring device 130 may comprise one or more buttons 140 and 142 for controlling the functions or operation of the electronic unit 134, in accordance to one embodiment of the present invention. The first button 140 may turn the weight-measuring device 130 on and off. The second button 142 may be configured to allow for a measurement unit to be selected to indicate the weight of the individual, e.g., pounds or kilograms.

Referring now to FIGS. 16-21, an alternate embodiment of the present invention is disclosed, the alternate embodiment comprises a germicidal sterilization apparatus 210 comprising a housing 220, a plate 230 secured to or formed integral with the housing 220 for supporting an individual thereatop, a base plate 240, and at least one electromagnetic light source 260 supported by the housing 220, the at least one electromagnetic light source 260 is shown herein as at least one UV light source 260*a*. In further accordance to this alternate embodiment, the at least one electromagnetic light source 260 may comprise an IR light source.

The apparatus 210 further comprises a central processing unit (CPU) 300, memory 310 and a storage device(s) 314 such as a hard disk and a portable storage device(s), the CPU 300, memory 310 and the storage device 314 coupled to communicate with one another, the plate 230 being coupled to the CPU 300 and memory 310 and in communication therewith. The apparatus 210 includes a power source 280 for supplying power, such as an electrical plug-in, a battery or series of batteries, solar, or some other suitable means for providing the electrical input required to power and operate the apparatus 210.

The plate 230 is defined as a UV-transparent or UV-transmissive flexible substrate 232 being suitably rigid and durable so as to support individuals thereatop. The flexible substrate 232 has a first UV-transparent or UV-transmissive conductive layer 234 located on the transparent flexible substrate 232. A flexible UV-transparent or UV-transmissive transparent cover panel 236 having a second UV-transparent or UV-transmissive conductive layer 238 and integral compressible UV-transparent or UV-transmissive spacer dots 240 formed in the flexible transparent cover panel 236 is located above the transparent flexible substrate 232. The integral compressible spacer dots 240 and flexible cover panel 236 may be injection roll molded unitarily.

Figure 19:
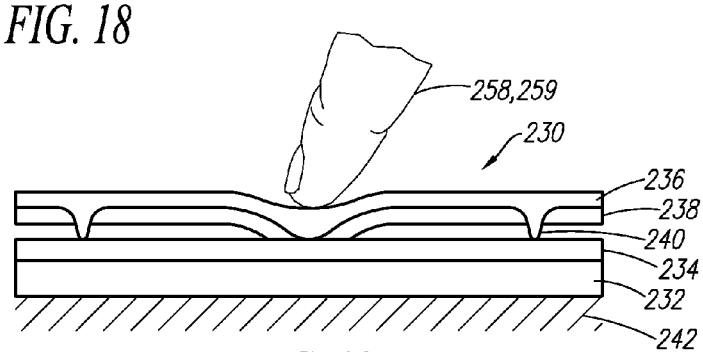
FIG. 19 is a side elevational view illustrating the operation of the plate shown in FIG. 18.
Figure 20:
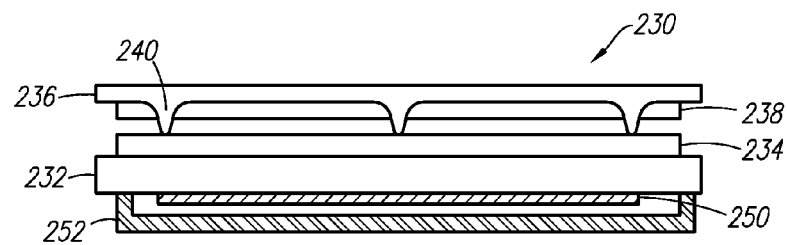
FIG. 20 is a side elevational view of the plate of the alternate embodiment shown integrated with a lower light emitting diode materials.
Figure 21:
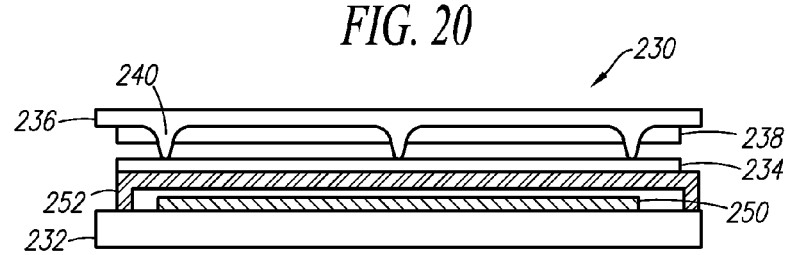
FIG. 21 is a side elevational view of the plate of the alternate embodiment shown integrated with an upper light emitting diode materials.

Referring now more particularly to FIGS. 19-21, in operation, the flexible substrate 232 has less flexibility than the flexible cover panel 236, or may be supported, for example, by a backing medium 242 (shown in FIG. 19) or organic light emitting diode (OLED) materials 250 and an encapsulating cover 252 (shown in FIG. 20). Alternatively, OLED materials 250 and an encapsulating cover 252 may be located between flexible substrate 232 and first conductive layer 234, as shown in FIG. 21.

When an external object 258, such as a finger 259 or stylus deforms the flexible transparent cover panel 236, the flexible transparent cover panel 236 is pressed against the flexible transparent substrate 232, thereby causing the first and second conductive layers 234 and 236 to touch and close a circuit. In the event deformation occurs on one of the integral compressible spacer dots 240, the spacer dot 240 is compressed so that contact is made between first and second conductive layers 234 and 236 and current flows therebetween. The at least one UV light source 260 being in operative communication with the plate 230, the plate 230 is adapted and configured so as to allow a user to activate the at least one UV light source 260 by inputting data via the touch sensitive plate 230.

Referring again to FIGS. 16-21, the apparatus 210 may further comprise a weight-measuring device 270, the weight-measuring device 270 being coupled to the memory and in communication therewith. The weight-measuring device 270 being in operative communication with the plate 230, wherein the weight-measuring device 270 may be activated by inputting data via the touch sensitive plate 230 for determining and indicating the weight of a desired article, object, or preferably, an individual.

Figure 22:
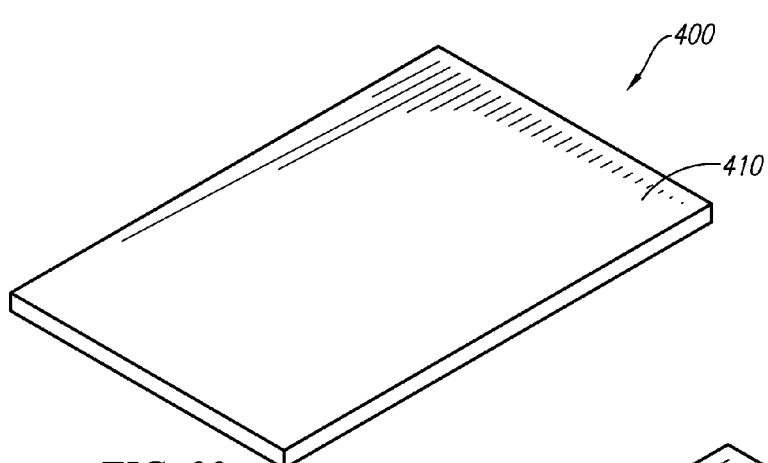
FIG. 22 is a perspective view of another alternate embodiment of the present invention.

Referring now to FIG. 22, in accordance to another embodiment of the present invention, a germicidal sterilization system 400 is disclosed, wherein the system 400 comprises photovoltaic glass 410 defined as highly efficient, thermally durable and flexible. The photovoltaic glass 410 may be suitably disposed in a photovoltaic glass support structure for balanced placement atop a horizontal surface, or inset within a planar support structure, such as flooring. The photovoltaic glass 410 may also be adapted for mounting to a vertical surface, such as a wall and/or ceiling, or inset therein.

The photovoltaic glass 410 may also be characterized as a lightweight panel, plate, or tablet, sizably configured and dimensioned to facilitate portability thereof. Particularly, it is envisioned such lightweight, photovoltaic glass 410 plate embodiment may be sized so as to be easily stored within a conventional laptop computer case/bag, briefcase, or travel case/bag.

The photovoltaic glass 410 is further defined as being display enabling, scratch and smudge resistant, and optically versatile.

The photovoltaic glass 410 is still further defined as being touch sensitive for enabling electronics and various applications which include, but are not limited to: IR light source generation; UV light source generation; weight measurement; timer settability; motion detection; pressure detection; biometric identification; electronic written, verbal, image, and video communication transmission; and audio, visual and tactile indication.

Generation of the UV light source generates UV light waves which kill or deactivate harmful germs (e.g., bacteria, viruses, mold, fungi, parasites, and spores thereof), microorganisms and spores thereof, pathogens, and/or transmissible diseases, thereby preventing the harmful germs, microorganisms and spores thereof, pathogens, and/or transmissible diseases from spreading and causing harm to other individuals.

Generation of the IR light source generates IR light which is administered to patients to prevent scar tissue formation, inflammation, and degenerative osteoarthritis. In addition, the IR light promotes wound healing and pain relief for scars, arthritis, fibromyalgia, sprains, headaches, diabetic ulcers, neuralgia, bursitis, sinsusitis, tennis elbow, temporomandibular joint disorder (TMJ), carpal tunnel, inflammation, edema, skin care, and the like. The use of IR light therapy also aids in preventing bone and muscle atrophy.

In accordance to yet another embodiment, the germicidal sterilization system 400 may be defined as modular, wherein the photovoltaic glass 410 is provided as a plurality of photovoltaic glass 410 panels suitably disposed about an enclosure, such as a room. The plurality of photovoltaic glass 410 panels are envisioned as being disposed along an entire floor, walls, and ceiling of the room. Using the touch sensitive surface of any one of the photovoltaic glass 410 panels, user may actuate generation of IR light waves and/or UV light waves, wherein the infrared light waves and/or UV light waves are projected from the panels omnidirectional about the room in such a manner so as to sterilize a target, e.g., a human.

Generation of such IR light waves and/or UV light waves, in accordance to this modular embodiment, may alternatively be actuated via other applications which include, but are not limited to: motion detection; pressure detection; biometric identification; and/or electronic written, verbal, and/or image communication transmission.

It is envisioned the above-described photovoltaic glass 410 and photovoltaic glass 410 panels may comprise a curved configuration.

Figure 23:
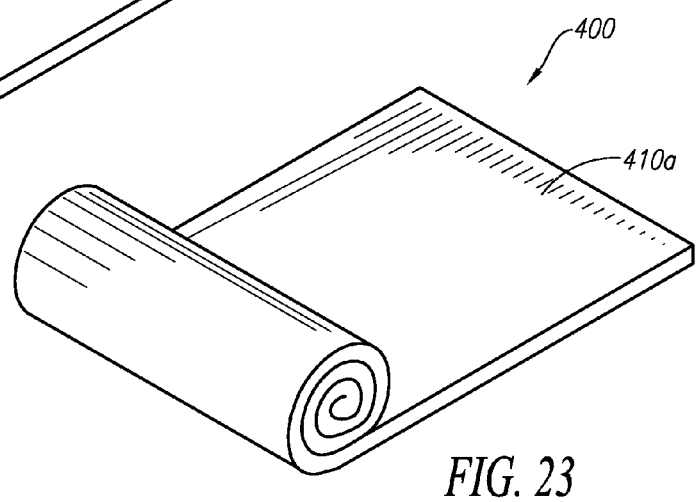
FIG. 23 is perspective view of still another alternate embodiment of the present invention.

Finally, with respect to FIG. 23, and in accordance to still another embodiment of the present invention, the photovoltaic glass 410a is defined as being lightweight, flexible and rollable to a compact size. The photovoltaic glass 410a is further defined as being water-resistant. The rollable photovoltaic glass 410a comprises the following capabilities, features, and functionalities: display enabling; scratch and smudge resistant; optically versatile; and touch sensitive for enabling electronics and various applications. Said electronics and applications include, but are not limited to: IR light source generation; UV light source generation; weight measurement; timer settability; motion detection; pressure detection; biometric identification; electronic written, verbal, image, and video communication transmission; and audio, visual and tactile indication.

It is envisioned that the various embodiments, as separately disclosed, are interchangeable in various aspects, so that elements of one embodiment may be incorporated into one or more of the other embodiments, and that specific positioning of individual elements may necessitate other arrangements not specifically disclosed to accommodate performance requirements or spatial considerations. It is to be understood that the embodiments and claims are not limited in its application to the details of construction and arrangement of the components set forth in the description and illustrated in the drawings. Rather, the description and the drawings provide examples of the embodiments envisioned, but the claims are limited to the specific embodiments. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the U.S. Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. It is intended that the application is defined by the claims appended hereto.

What is claimed is:

1. A germicidal sterilization apparatus, the apparatus comprising:
a housing;
a planar plate disposed atop the housing, the planar plate includes an upper surface opposing a lower surface, the upper surface defining a target surface;
a base plate;
at least one electromagnetic light source supported by the housing; and a power source for supplying power to the at least one electromagnetic light source.

2. The apparatus of claim 1, wherein the at least one electromagnetic light source generates UV light waves which kill or deactivate harmful germs, microorganisms and spores thereof, pathogens, and/or transmissible diseases.

3. The apparatus of claim 1, wherein the planar plate is UV-transparent or UV-transmissive, and suitably rigid and durable so as to support an individual thereatop.

4. The apparatus of claim 1, wherein the housing comprises a vessel wall having a bottom from which an arched sidewall extends upwardly therefrom, the bottom and the arched sidewall each include a UV reflective interior surface.

5. The apparatus of claim 4, wherein the housing defines an interface, the interface joining the UV reflective interior surface and an outer circumferential surface of the arched sidewall of the housing.

6. The apparatus of claim 4, wherein the housing includes an area between the UV reflective interior surface and the planar plate defined as a UV light source cavity within which the at least one electromagnetic light source is enclosed.

7. The apparatus of claim 5, wherein the housing having the planar plate disposed thereatop, the plate being shaped and configured to match a shape and configuration of the interface of the housing.

8. The apparatus of claim 4, wherein the housing further comprising a UV lamp holder, the UV lamp holder removably holds the at least one electromagnetic light source, the at least one electromagnetic light source is in electrical connection with the UV lamp holder, the UV lamp holder being electrically connected to the power source.

9. The apparatus of claim 1, wherein the apparatus further comprising control electronics for selectively-controlling activation of the at least one electromagnetic light source.

10. The apparatus of claim 9, wherein the control electronics comprises an ON/OFF switch.

11. The apparatus of claim 10, wherein the ON/OFF switch is suitably mounted to the housing.

12. The apparatus of claim 10, wherein the ON/OFF switch is disposed in a remote, wired hand-held device, the remote wired device is in electrical communication with the at least one electromagnetic light source.

13. The apparatus of claim 10, wherein the ON/OFF switch is disposed in a remote, wireless hand-held device, the remote wireless hand-held device is in wireless, electrical communication with the at least one electromagnetic light source.

14. The apparatus of claim 9, wherein the control electronics comprises a motion detector for detecting the presence of a user atop the planar plate.

15. The apparatus of claim 9, wherein the control electronics comprises a timer for de-energizing the at least one electromagnetic light source upon the expiration of a predetermined interval of time.

16. The apparatus of claim 2, wherein the at least one electromagnetic light source comprises a plurality of UV lamp tubes.

17. The apparatus of claim 16, wherein the plurality of UV lamp tubes comprises UV-C lamp tubes.

18. The apparatus of claim 16, wherein the plurality of UV lamp tubes comprises UV-C lamp tubes, and UV-A lamp tubes and/or UV-B lamp tubes.

19. The apparatus of claim 9, wherein the apparatus further comprising an electronic weight-measuring device for determining and indicating the weight of an individual.

20. The apparatus of claim 19, wherein the electronic weight-measuring device comprises:
a weight sensor, the weight sensor defining a weight-dependent property;
an electronic unit, the electronic unit obtains and processes the weight-dependent property of the weight sensor in order to determine a weight of an individual; and
a display for displaying the weight of an individual, wherein the electronic unit outputs signals to the display in order to display the weight of the individual.

21. A germicidal sterilization apparatus, the apparatus comprising:
a housing;
a planar plate disposed atop the housing;
a base plate;
at least one electromagnetic light source supported by the housing;
a CPU;
a memory;
at least one storage device, the CPU, the memory and the at least one storage device coupled to communicate with one another, the plate being coupled to the CPU and the memory and in communication therewith; and
a power source for supplying an electrical input required to power and operate the apparatus.

22. The apparatus of claim 21, wherein the plate is defined as a touch sensitive plate, the at least one electromagnetic light source being in operative communication with the plate, the plate is configured so as to allow a user to activate the at least one electromagnetic light source by inputting data via the touch sensitive plate.

23. The apparatus of claim 22, wherein the plate comprises a UV-transparent or UV-transmissive flexible substrate being suitably rigid and durable so as to support individuals thereatop.

24. The apparatus of claim 23, wherein the UV-transparent or UV-transmissive flexible substrate has a first UV-transparent or UV-transmissive conductive layer located on the UV-transparent or UV-transmissive flexible substrate, the UV-transparent or UV-transmissive flexible substrate has a flexible UV-transparent or UV-transmissive transparent cover panel located thereabove, the flexible UV-transparent or UV-transmissive transparent cover panel has a second UV-transparent or UV-transmissive conductive layer and integral compressible UV-transparent or UV-transmissive spacer dots formed in the flexible transparent cover panel.

25. The apparatus of claim 24, wherein the flexible transparent cover panel is depressible or deformable to press against the UV-transparent or UV-transmissive flexible substrate, thereby causing the first UV-transparent or UV-transmissive conductive layer and the flexible UV-transparent or UV-transmissive transparent cover panel to touch and close a circuit, and whereupon deformation occurs on one of the integral compressible UV-transparent or UV-transmissive spacer dots, the spacer dot is compressed so that contact is made between the first UV-transparent or UV-transmissive conductive layer and the flexible UV-transparent or UV-transmissive transparent cover panel and current flows therebetween.

26. The apparatus of claim 21, wherein the apparatus further comprising a weight-measuring device.

* * * * *